US011129937B2

United States Patent
Jugl et al.

(10) Patent No.: US 11,129,937 B2
(45) Date of Patent: Sep. 28, 2021

(54) NEEDLE ASSEMBLY AND DRUG DELIVERY DEVICE HAVING SUCH NEEDLE ASSEMBLY

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE); Stefan Blancke, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 294 days.

(21) Appl. No.: 16/093,184

(22) PCT Filed: Apr. 13, 2017

(86) PCT No.: PCT/EP2017/058990
§ 371 (c)(1),
(2) Date: Oct. 12, 2018

(87) PCT Pub. No.: WO2017/178616
PCT Pub. Date: Oct. 19, 2017

(65) Prior Publication Data
US 2019/0117887 A1    Apr. 25, 2019

(30) Foreign Application Priority Data
Apr. 14, 2016   (EP) ..................... 16165373

(51) Int. Cl.
*A61M 5/168* (2006.01)
*A61M 5/162* (2006.01)
(Continued)

(52) U.S. Cl.
CPC .......... *A61M 5/16831* (2013.01); *A61J 1/201* (2015.05); *A61M 5/162* (2013.01);
(Continued)

(58) Field of Classification Search
CPC .............. A61M 5/16831; A61M 5/162; A61M 5/3293; A61M 2005/1588;
(Continued)

(56) References Cited

U.S. PATENT DOCUMENTS

| 4,384,578 A | * | 5/1983 | Winkler ............ A61M 5/16886 128/DIG. 13 |
| 2007/0219480 A1 | * | 9/2007 | Kamen ................ A61B 5/1427 604/20 |

(Continued)

FOREIGN PATENT DOCUMENTS

| WO | WO 02/07808 | 1/2002 |
| WO | WO 2008/114218 | 9/2008 |

(Continued)

OTHER PUBLICATIONS

Chothia et al., "Canonical structures for the hypervariable regions of immunoglobulins," Journal of Molecular Biology 196(4):901-917, Aug. 20, 1987.

(Continued)

*Primary Examiner* — Nathan R Price
*Assistant Examiner* — Justin L Zamory
(74) *Attorney, Agent, or Firm* — Fish & Richardson P.C.

(57) ABSTRACT

Described herein are specialized needle assemblies for injection systems. One example injection system includes a needle assembly configured to removably attach to a drug delivery device and a housing configured to receive a drug cartridge. The needle assembly includes a needle configured to extend through an outlet port of the drug delivery device and establish fluid communication with the drug cartridge within the housing of the drug delivery device. The needle assembly may include a fluid flow sensor monitoring the fluid flow and/or occlusions within the needle assembly, and provide indications of an occluded or clogged needle and/or (Continued)

one or more indications of proper flow through the needle, e.g., non-occlusion of the needle. In some examples, the arrangement of the needle assembly includes sensors to detect an occlusion within a portion of a needle.

14 Claims, 2 Drawing Sheets

(51) Int. Cl.
    *A61J 1/20*     (2006.01)
    *A61M 5/32*     (2006.01)

(52) U.S. Cl.
    CPC ........ *A61M 5/3293* (2013.01); *A61J 2200/70* (2013.01); *A61M 2005/16863* (2013.01); *A61M 2202/07* (2013.01); *A61M 2205/3306* (2013.01); *A61M 2205/3334* (2013.01); *A61M 2205/581* (2013.01); *A61M 2205/582* (2013.01); *A61M 2205/583* (2013.01)

(58) Field of Classification Search
    CPC ......... A61M 2005/16863; A61M 2005/16868; A61M 2005/16872; A61M 2205/3306; A61M 2205/3334; A61M 2205/581; A61M 2205/582; A61M 2205/583; A61M 5/158
    See application file for complete search history.

(56) References Cited

U.S. PATENT DOCUMENTS

| | | | |
|---|---|---|---|
| 2009/0306594 A1* | 12/2009 | Pang | A61F 9/0017 604/133 |
| 2013/0178792 A1* | 7/2013 | Li | A61M 5/14566 604/67 |
| 2014/0114238 A1* | 4/2014 | Lee | A61M 5/172 604/67 |
| 2014/0276578 A1 | 9/2014 | Bullington et al. | |

FOREIGN PATENT DOCUMENTS

| | | |
|---|---|---|
| WO | WO 2011/020201 | 2/2011 |
| WO | WO 2012/037428 | 3/2012 |

OTHER PUBLICATIONS

Hwang et al., "Use of human germline genes in a CDR homology-based approach to antibody humanization," Methods 36(1):35-42, May 2005.

International Preliminary Report on Patentability in International Application No. PCT/EP2017/058990, dated Oct. 16, 2018, 6 pages.

International Search Report and Written Opinion in International Application No. PCT/EP2017/058990, dated Jul. 5, 2017, 9 pages.

Jones et al., "Replacing the complementarity-determining regions in a human antibody with those from a mouse," Nature 321(6069):522-525, May 1986.

Kabat, et al., "Unusual distributions of amino acids in complementarity determining (hypervariable) segments of heavy and light chains of immunoglobulins and their possible roles in specificity of antibody-combining site," Journal of Biological Chemistry 252(19):6609-6616, Oct. 1977.

MacCallum et al., "Antibody-antigen interactions: contact analysis and binding site topography," Journal of Molecular Biology 262(5):732-745, Oct. 1996.

Orlandi et al., "Cloning immunoglobulin variable domains for expression by the polymerase chain reaction," Proceedings of the National Academy of Sciences U.S.A. 86(10):3833-3837, May 1989.

Queen et al., "A humanized antibody that binds to the interleukin 2 receptor," Proceedings of the National Academy of Sciences U.S.A. 86(24):10029-10033, Dec. 1989.

Riechmann et al., "Reshaping human antibodies for therapy," Nature 332(6162):323-327, Mar. 1988.

Verhoeyen et al., "Reshaping human antibodies: grafting an antilysozyme activity," Science 239(4847):1534-1536, Mar. 1988.

* cited by examiner

NEEDLE ASSEMBLY AND DRUG DELIVERY DEVICE HAVING SUCH NEEDLE ASSEMBLY

CROSS REFERENCE TO RELATED APPLICATIONS

This application is a U.S. national stage application under 35 USC § 371 of International Application No. PCT/EP2017/058990, filed on Apr. 13, 2017, which claims priority to European Application No. 16165373.8, filed on Apr. 14, 2016, the entire contents of which are incorporated herein by reference.

TECHNICAL FIELD

The disclosure relates to needle assemblies for drug delivery devices.

BACKGROUND

In injection devices, there is a trend toward the use of progressively smaller gauge needles typically used for self-injection. While small gauge needles typically reduce the pain associated with the procedure, their use can complicate drug delivery due to an increased risk of drug solidification within the needles. Drug formulations may further increase this risk.

SUMMARY

The present disclosure provides needle assemblies for drug delivery devices. A sensor configured to sense a flow condition of a fluid (e.g., a drug) is provided in and/or near a needle assembly of a drug delivery device.

The term "drug delivery device" shall be understood to encompass any type of device, system or apparatus designed to immediately dispense a drug, or a formulation containing a drug, to a human or non-human body (veterinary applications are clearly contemplated by the present disclosure). By "immediately dispense" is meant an absence of any necessary intermediate manipulation of the drug or drug formulation by a user between discharge of the drug or drug formulation from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems. The caps described herein are particularly useful with injection devices that include a hollow needle, which is used to introduce the drug into the human or non-human body. In particular, the injection device may be fitted for self-operated day-by-day administration of medication and may be filled with any injectable medicament, e.g., insulin, GLP-1, or heparin.

The needle assemblies described herein can be used in injection systems configured to deliver a desired drug dose to a patient via an injection or self-injection, using a relatively small gauge needle to reduce the pain associated with the procedure. Needle assemblies described herein can identify a clogged or blocked needle to help reduce the safety risks and the efficacy risks posed by a clogged needle (e.g., accidental injection of solidified drug into the user, device malfunction, and/or injection of an insufficient drug dosage). By doing so, the occluded needle assembly can be replaced, and the drug delivery device can continue to safely and reliably deliver a desired drug dosage.

An example is a vial spiking device including a housing substantially surrounding a needle and at least partially defining a cavity configured to receive a portion of a drug vial. The device includes a fluid flow sensor positioned adjacent to at least a portion of the needle within the housing.

In some examples, the housing further includes a central boss positioned within the housing and extending from an external surface of the housing. The central boss encloses at least a portion of the needle.

In some examples, at least a portion of the central boss includes a transparent material. In some examples, the central boss is non-metallic.

In some examples, the fluid flow sensor is positioned adjacent to the needle in a manner such that the fluid flow sensor is aligned with the transparent material of the central boss.

In some examples, the needle includes two coaxial needles axially separated by a detection section Another example is a drug delivery device including a housing substantially surrounding a needle and at least partially defining a cavity configured to receive a portion of a drug vial. The drug delivery device includes a drug vial positioned at least partly within the cavity, a fluid flow sensor positioned adjacent to at least a portion of the needle within the housing, and a control unit in communication with the fluid flow sensor.

In some examples, the drug vial houses a drug.

In some examples, the drug includes insulin, GLP-1, or both.

Other aspects, features, and advantages of the disclosed subject matter will be apparent from the description and drawings, and from the claims.

DETAILED DESCRIPTION

The present specification describes specialized needle assemblies for use with drug delivery devices. The needle assemblies are particularly useful in injection systems that include a needle assembly configured to removably attach to a drug delivery device and a housing configured to receive a drug cartridge, wherein the needle assembly includes a needle that can extend through an outlet port of the drug delivery device to establish fluid communication with the drug cartridge within the housing of the drug delivery device. As will be described in detail below, a fluid flow sensor 8 of a needle assembly is positioned within the needle assembly adjacent to a needle. The fluid flow sensor monitors the fluid flow (e.g., drug flow) and/or occlusions within the needle assembly, and provides one or more indications of an occluded or clogged needle and/or one or more indications of proper flow through the needle, e.g., non-occlusion of the needle.

Figure 1:
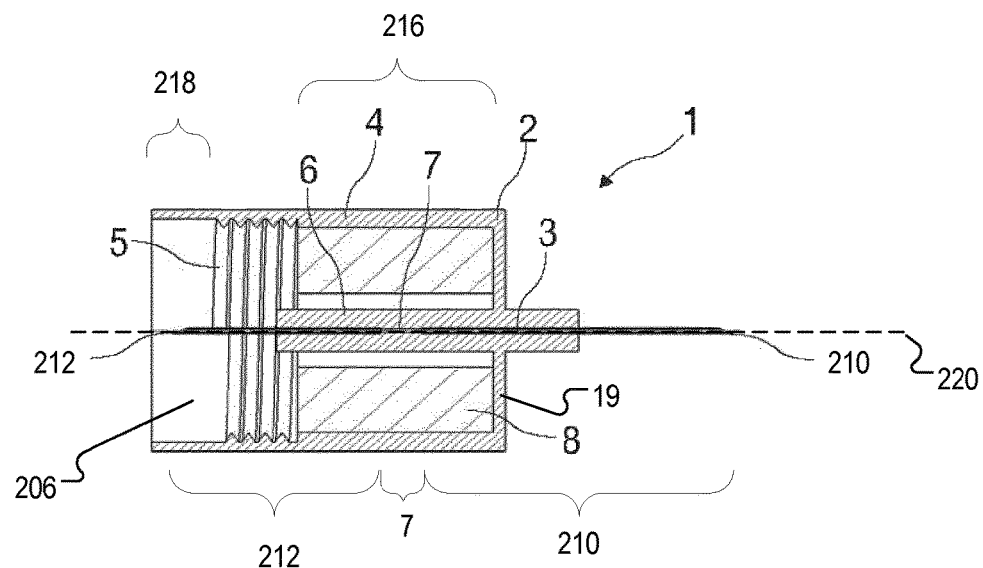
FIG. 1 is a schematic cross-sectional view of a needle assembly with a sensor.
Figure 2:
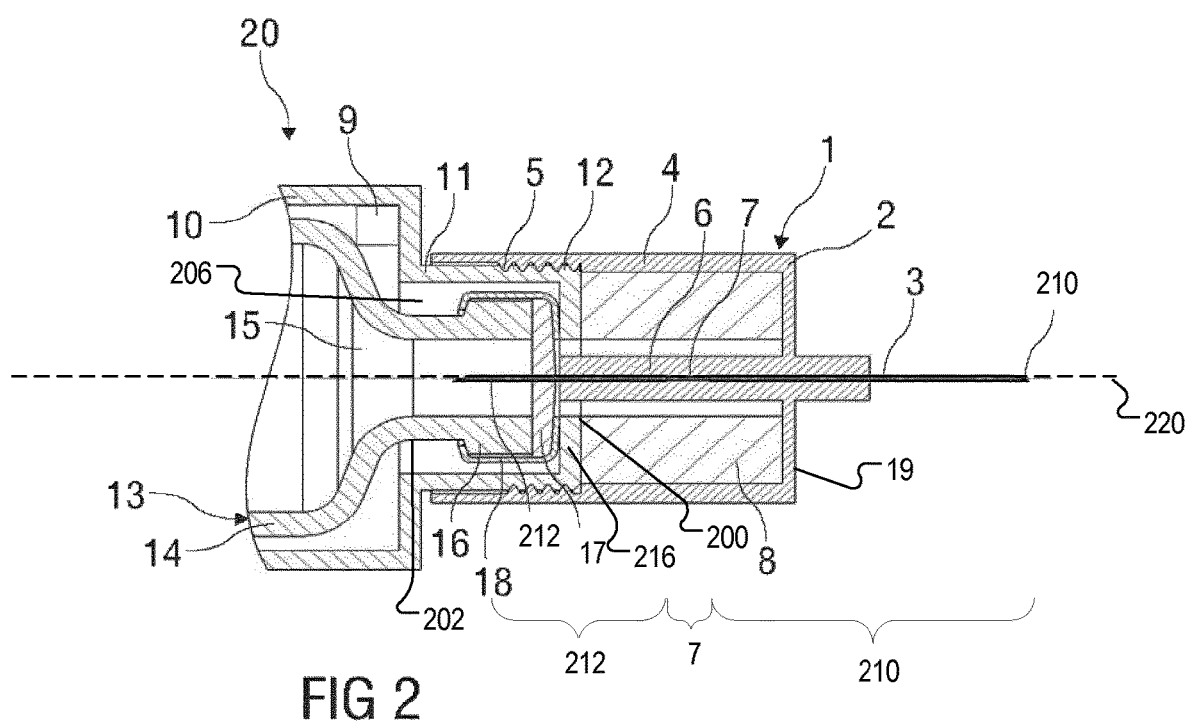
FIG. 2 is a schematic cross-sectional view of the needle assembly of FIG. 1 mounted to a cartridge holder.

In certain embodiments, the arrangement of the needle assembly includes one or more sensors to detect an occlusion within at least a portion of a needle. For example, FIG. 1 shows a needle assembly 1 that includes a needle hub 2 and a needle 3. The needle hub 2 has an outer cylindrical wall 4. The needle 3 (e.g., a double-ended hypodermic needle) is held within a boss 6 of the needle hub 2, and a fluid flow sensor 8 is arranged within the needle hub 2. The needle assembly can include internal threads 5 for engaging an external thread of a cartridge holder (as shown in FIG. 2).

As shown in FIG. 1, a boss 6 is positioned within the needle assembly 1 parallel to a longitudinal axis 220 of the needle assembly 1. The boss 6 extends through a distal wall 19 of the needle hub 2. For example, the boss 6 can overlap a portion of the internal threads 5 (e.g., a portion defined by an inner circumferential surface) and extend to beyond the distal wall 19. The boss 6 defines a channel extending through the boss 6. The needle 3 is positioned within the channel of the boss 6 such that the boss 6 prevents axial movement of the needle 3 relative to the boss 6. The needle 3 extends from the boss 6 at each end of the boss 6.

Still referring to FIG. 1, the needle 3 has a central passage in fluid communication with a cavity 206. The cylindrical wall 4 defines at least a portion of the cavity 206, which is configured to receive at least a portion of a drug cartridge and/or a drug cartridge holder when the needle assembly 1 is engaged with or part of a drug delivery device. When the cavity 206 is engaged with or part of a drug delivery device, the central passage of the needle 3 is fluidly connected with a drug cartridge and/or a drug cartridge holder. The needle 3 is formed of one or more medical grade plastics (e.g., PVC, acrylonitrile butadiene styrene (ABS). However, other medical grade plastics can be used to form the needle 3. Similarly, certain metals, such as stainless steel, could be used to form the needle 3. In some examples, the needle 3 can be formed from a combination of medical grade plastic and metal material.

As shown in FIG. 1, the needle 3 includes a distal needle portion 210 and a proximal needle portion 212, separated from each other by a detection section 7 between the distal needle portion 210 and the proximal needle portion 212. The detection section 7 is positioned distal to the internal threads 5 within a proximal assembly portion 218 of the needle assembly 1.

In some embodiments, the distal needle portion 210 and the proximal needle portion 212 are formed from separate needles axially separated by the detection section 7. In this example, the distal needle portion 210 and the proximal needle portion 212 are positioned within the boss 6 and fluidly connected within the boss 6. For example, the inner diameter of the boss 6 is about 98% of the outer diameter of the needle 3.

In some examples, the detection section 7 can be formed from a material that is different from the distal needle portion 210 and the proximal needle portion 212. Thus, the material of at least the detection section 7 can be formed of a material compatible with the fluid flow sensor 8. For example, the detection section 7 can be formed of a non-metallic material if the fluid flow sensor 8 is an optical sensor.

Referring to FIGS. 1 and 2, the fluid flow sensor 8 is positioned within the needle assembly 1 adjacent to the detection section 7. For example, the fluid flow sensor 8 is secured within the cartridge holder 2 a distal end 216 of the cartridge holder 10. The fluid flow sensor 8 generates and transmits a signal to a control unit 9 (e.g., a processor) within a drug delivery device 20. In some embodiments, the fluid flow sensor 8 and the control unit 9 can communicate via a wired or wireless connection. The fluid flow sensor 8 can additionally or alternatively include a passive transponder adapted to communicate with and be powered by a read/write unit of the control unit 9, an active transponder including a battery, or a combination of passive and active transponders.

The fluid flow sensor 8 detects fluid flow conditions (e.g., a fluid flow or a lack thereof). As a result, the fluid flow sensor 8 can help to determine whether the drug is flowing through the needle 3. In some implementations, the fluid flow sensor 8 is an optical sensor. Other types of sensors can alternatively or additionally be used, such as sensors using ultrasonic, magnetic or electrostatic technology. In some implementations, the fluid flow sensor 8 can sense the presence of a drug within the needle itself or can detect an air bubble or a solid mass within the detection section 7.

The boss 6 can be formed of a sterilizable material (e.g., polyethylene (PE), high density polyethylene (HDPE)). For example, if the fluid flow sensor 8 is an optical sensor, the boss 6 can be formed from a transparent material (e.g., a plastic material). In some cases, the boss 6 is formed from a single material. In some implementations, at least a portion of the boss 6 positioned adjacent to the detection section 7 is additionally or alternatively formed from a material compatible with the fluid flow sensor 8 so that the fluid flow sensor 8 can monitor flow conditions within the needle 3 through the boss 6.

Referring to FIG. 2, the drug delivery device 20 includes a cartridge holder 10 having a cavity for receiving a drug cartridge 13. The drug cartridge 13 has a cavity 15 and a septum 17. A ferrule 18 partially encloses the septum 17 and is permanently or releasably fixed to a portion of the drug cartridge 13. This arrangement secures the septum 17 to the drug cartridge 13. The distal end 216 of the cartridge holder 10 includes an adapter 11 for securing the needle assembly 1 to the cartridge holder 10. The adapter 11 includes external threads 12 for engaging the internal threads 5 of the needle assembly 1. This arrangement allows the needle 3 to pierce the septum 17, thereby establishing a fluid communication between the cavity 15 and the needle 3. For example, the needle hub 2 is connected to the adapter 11 until the adapter 11 is adjacent to or abuts the fluid flow sensor 8 to form an interface 200. In this position, a tip of the proximal needle portion 212 of the needle 3 pierces the septum 17 to establish a fluid communication between the cavity 15 and the needle 3. In some cases, fluid communication is additionally or alternatively established between the cavity and at least a portion of the channel within the boss 6.

During use, the control unit 9 can generate an indication that a fluid within the detection section 7 is not flowing or that the needle assembly 1 is clogged. For example, the control unit 9 can generate a visual, audible, and/or tactile indication if the fluid flow sensor 8 detects that the fluid within the detection section 7 is stagnant or unexpectedly reduced or if the fluid flow sensor 8 detects an occlusion in the detection section 7, thus indicating a clogged or blocked needle 3. The control unit 9 can also be arranged to prevent a delivery mechanism (not illustrated) from functioning if the fluid flow sensor 8 senses abnormal fluid flow within the detection section 7 (e.g., by locking a manually or spring operated plunger for displacing the fluid from the cartridge in position or by stopping or preventing operation of a motor for advancing the plunger). If the needle assembly 1, with the clogged or blocked needle 3, is subsequently replaced by a new needle assembly, the fluid flow sensor 8 can detect normal flow conditions and the control unit 9 can resume drug delivery (e.g., by unblocking the delivery mechanism such that an injection may be performed or continued).

In some embodiments, the control unit 9 can additionally or alternatively generate an indication that fluid within the device (e.g., the needle 3) is flowing normally or as expected. If the drug delivery device 20 fails to indicate normal flow, the control unit 9 can prevent a delivery mechanism from functioning.

Prior to use of the drug delivery device 20, the drug cartridge 13 is inserted into the cartridge holder 10 as shown in FIG. 2. In this position, the septum 17 abuts the boss 6 of the needle assembly 1 so that the needle assembly 1 is disposed over the adapter 11. The cartridge holder 10 and the needle assembly 1 are individually or cooperatively rotated to engage the threads of the adapter 11 with the internal threads 5 of the needle assembly 1 to cause the needle assembly 1 to move along the adapter 11 towards the center of the cartridge holder 10. Rotating the cartridge holder 10 or the needle assembly 1 can create a fluid-tight seal between the needle assembly 1 and the adapter 11. At this point, the needle 3 of the needle assembly 1 pierces the septum 17 of the drug cartridge 13.

After attaching the needle assembly 1 to the cartridge holder 10, the user can begin drug delivery. During drug delivery, the fluid flow sensor 8 senses the flow conditions within the drug delivery device (e.g., the needle) and transmits fluid flow information to the control unit 9. The control unit 9 monitors the fluid flow information to determine if the needle is clogged or occluded. In some examples, the user will receive an indication, such as audio and/or visual signal and/or tactile feedback if the needle 3 is clogged. In some drug delivery devices, the drug delivery device 20 will be inoperable until the fluid flow sensor 8 and the control unit 9 identify normal or expected flow conditions.

While certain embodiments have been described, other embodiments are possible.

Figure 3:
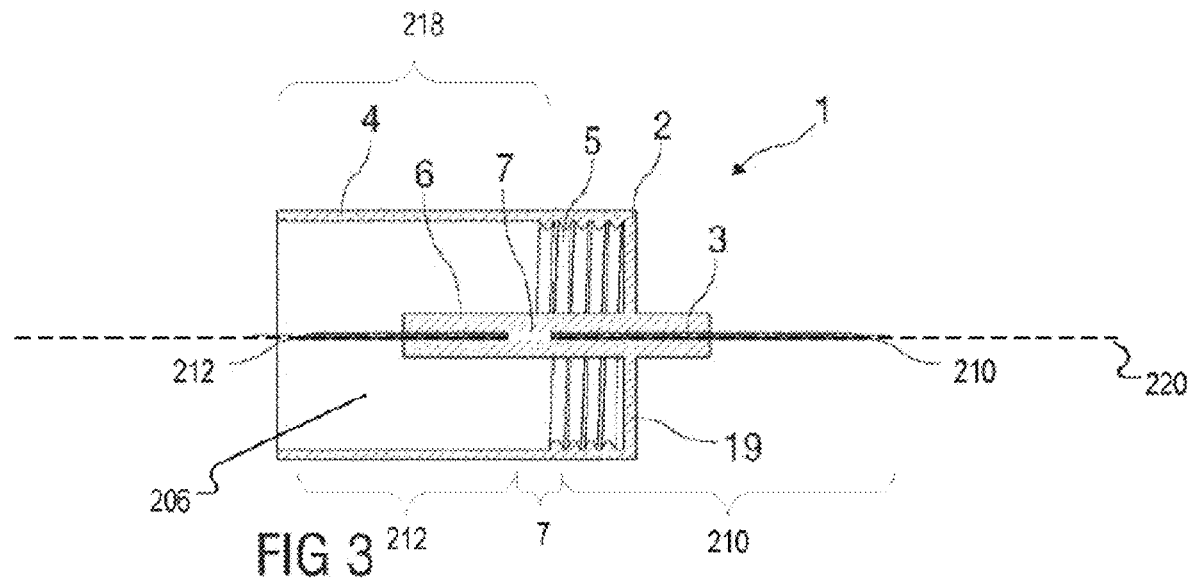
FIG. 3 is a schematic cross-sectional view of another embodiment of a needle assembly.
Figure 4:
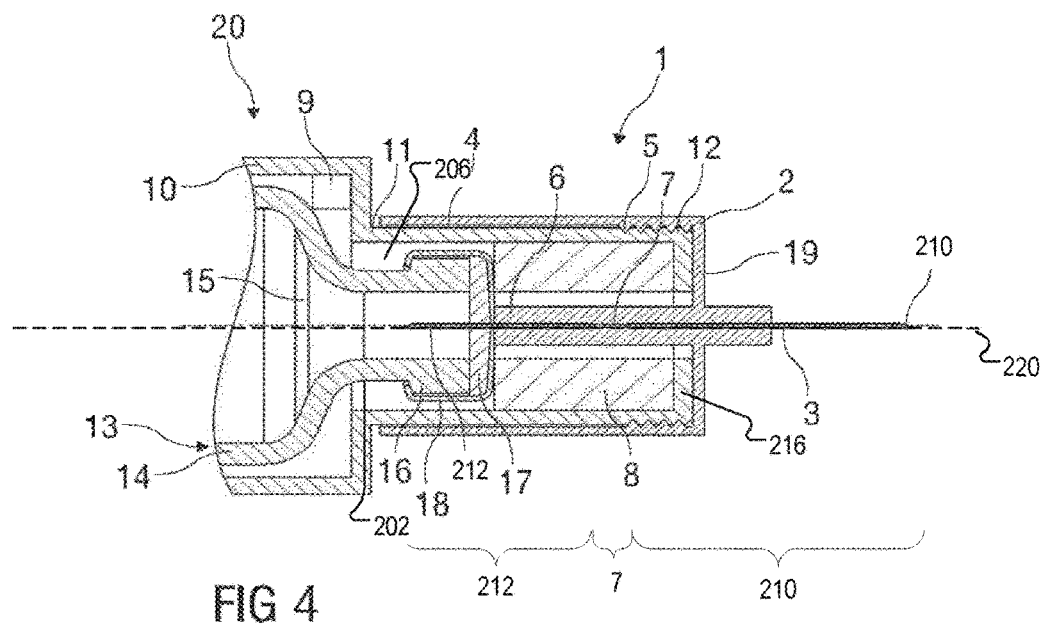
FIG. 4 is a schematic cross-sectional view of the needle assembly of FIG. 3 mounted to a cartridge holder.

Referring to FIGS. 3 and 4, the boss 6 of the needle assembly 1 can extend into the cavity 206. As such, at least a portion of the boss 6 is positioned within the cartridge holder 10 (e.g., into the adapter 11). For example, more than 50% of the total axial length can be positioned within the adapter 11 when the needle assembly 1 is connected to the cartridge holder 10. This arrangement allows the needle 3 to pierce the septum 17, thereby establishing a fluid communication between the cavity 15 and the needle 3. For example, the needle hub 2 is connected to the adapter 11 until the adapter 11 is adjacent to or abuts a distal wall 19 of the needle assembly 1. In this position, a tip of the proximal needle portion 212 of the needle 3 pierces the septum 17 to establish a fluid communication between the cavity 15 and the needle 3.

In some embodiments, the cartridge holder 10 can additionally or alternatively include the fluid flow sensor 8. For example, as shown in FIG. 4, the adapter 11 of the cartridge holder 10 can include the fluid flow sensor 8. The fluid flow sensor 8 can be positioned between a neck 202 of the drug cartridge 13 and a distal wall 19 of the cartridge holder 10 (e.g., distal to the internal threads 5) as shown in FIG. 4.

Still referring to FIG. 4, in some embodiments, the detection section 7 can alternatively or additionally be positioned within the cavity 206. This arrangement positions the fluid flow sensor 8 within the cartridge holder 10 to be positioned adjacent to the detection section 7. In this implementation, the detection section 7 is within the cavity 206. This arrangement positions the fluid flow sensor 8 adjacent to the detection section 7 when the needle assembly 1 engages with the cartridge holder 10.

While a single fluid flow sensor 8 has generally been described, in some embodiments the drug delivery device can alternatively or additionally include two or more fluid flow sensors positioned in the drug delivery device to detect fluid flow. For example, multiple fluid flow sensors can be positioned at various locations along the needle 3 and/or along one or more portions of the cartridge holder 10 and/or the drug cartridge 13.

While a single detection section 7 has generally been described, in some embodiments, the needle assembly 1 can alternatively or additionally include more than one detection section along a fluid path within the drug delivery device. For example, the needle 3 can include at least 2 (e.g., 2, 3, 4, 5, or 6) detection sections. In some embodiments, one or more detection sections can alternatively or additionally be positioned adjacent to a portion of the drug cartridge. In this arrangement, fluid flow through multiple portions of the drug delivery device can be monitored.

While the control unit 9 is generally described as positioned within the drug delivery device 20, in some embodiments the control unit 9 can additionally or alternatively be configured as an external unit (e.g., a separate device and/or a positioned on an external surface of the drug delivery device).

While the needle assembly 1 is generally described as including internal threads, in some embodiments, the needle assembly 1 is additionally or alternatively connected to the cartridge holder 10 using another removable connection technique (e.g., an interference fit, a snap fit, and/or a weak adhesive).

The drug delivery device and needle assemblies described herein are particularly useful for increasing the safety of drug delivery devices, such as injection devices, and/or for increasing the efficacy with which a drug is delivered to a human or non-human body using such devices. For self-injection devices, such as insulin injectors, a small gauge needle is desirable because smaller gauges typically result in less pain to the user upon injection. However, a risk associated with needles, especially smaller gauge needles, is that the needle can become partially or completely occluded due to solidification of the drug in the inner bore of the needle. Occlusion may occur, for example, if the needle is left in-situ following use or if a user fits a needle to the device for later use, rather than immediate injection. Skilled practitioners will appreciate that an occluded needle may pose a safety risk to a user in any number of ways, e.g., by causing accidental injection of solidified drug into the user. Skilled practitioners will also appreciate that an occluded needle can affect the efficacy of the treatment, e.g., causing malfunctioning of the device and too small of the dose being administered to the user.

Partial or complete occlusion of needles is of particular concern with certain drugs described herein. Such drugs, which may be in water-based formulations and at relatively high concentrations, may be at risk of solidifying in particular storage situations. One non-limiting example is high concentration insulin formulations described in further detail below.

The terms "drug" or "medicament" which are used interchangeably herein, mean a pharmaceutical formulation that includes at least one pharmaceutically active compound. Exemplary pharmaceutically active compounds include small molecules; polypeptides, peptides and proteins (e.g., hormones, growth factors, antibodies, antibody fragments, and enzymes); carbohydrates and polysaccharides; and nucleic acids (e.g., oligonucleotides, double or single stranded DNA (including naked and cDNA), RNA, antisense nucleic acids such as antisense DNA and RNA, small interfering RNA (siRNA), and ribozymes, and genes). Nucleic acids may be incorporated into delivery systems such as vectors, plasmids, or liposomes. Mixtures of any drugs described herein are contemplated. The presently described caps are particularly useful with injection devices that include a needle, e.g., a small gauge needle, and a drug for treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

Insulin formulations can be used in such an injection device for treatment and/or prophylaxis of diabetes mellitus. An insulin formulation can include, e.g., human insulin, or a human insulin analogue or derivative, glucagon-like peptide (GLP-1) or an analogue or derivative thereof, or exendin-3 or exendin-4 or an analogue or derivative of exendin-3 or exendin-4, or any mixture thereof.

Exemplary insulin analogues are Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4, for example, can be Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro- Ser-Ser-Gly-Ala-Pro-Pro-Pro-Ser-NH2.

Examples of Exendin-4 derivatives include: H-(Lys)4-des Pro36, des Pro37 Exendin-4(1-39)-NH2, H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative; or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu) 5-des Pro36, Pro37, Pro38 [Asp28] Exendin-4(1-39)-(Lys) 6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met (O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2; or a pharmaceutically acceptable salt or solvate of any one of the afore-mentioned Exendin-4 derivatives.

Exemplary hormones are include hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include, for example, a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

The presently described caps may also be used to help protect an injection needle from occlusion wherein the drug is an antibody. The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume 1 (Springer Protocols)* (Springer; 2nd ed., May 21, 2010); Lo, *Antibody Engineering: Methods and Protocols (Methods in Molecular Biology)* (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

The term "chimeric antibody" refers to an antibody that has been engineered to comprise at least one human constant region. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies and will also be aware of suitable techniques for their generation.

The term "humanized antibody" refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized antibodies are known in the art, and suitable techniques for generating humanized antibodies are also known. See for example, Hwang et al., *Methods* 36:35, 2005; Queen et al., *Proc. Natl. Acad. Sci. U.S.A.* 86:10029-10033, 1989; Jones et al., *Nature* 321:522-25, 1986; Riechmann et al., *Nature* 332:323-27, 1988; Verhoeyen et al., *Science* 239:1534-36, 1988; and Orlandi et al., *Proc. Natl. Acad. Sci. U.S.A.* 86:3833-3837, 1989.

The term "fully human antibodies" are antibodies or antigen binding fragments of antibodies that include only human-derived amino acid sequences. For example, a fully human antibody may be produced from a human B-cell or a human hybridoma cell. In additional embodiments, the antibody may be produced from a transgenic animal that contains the locus for a human heavy chain immunoglobulin and a human light chain immunoglobulin, or contains a nucleic acid that encodes the heavy and light chains of a specific human antibody.

The terms "Complementarity-determining region" or "CDR" refer to short polypeptide sequences within the variable region of both heavy and light chain polypeptides that are primarily responsible for mediating specific antigen recognition. CDRs have been described by Kabat, et al., *J. Biol. Chem.* 252, 6609-6616, 1977; Chothia et al., *J. Mol. Biol.* 196:901-917, 1987; and MacCallum et al., *J. Mol. Biol.* 262:732-745, 1996. There are three CDRs (termed CDR1, CDR2, and CDR3) within each VL and each VH.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments can include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The term "Framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion $N+(R1)(R2)(R3)(R4)$, wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES

| | |
|---|---|
| needle assembly | 1 |
| needle hub | 2 |
| needle | 3 |
| cylindrical wall | 4 |
| internal thread | 5 |
| detection section | 7 |
| fluid flow sensor | 8 |
| control unit | 9 |

| | |
|---|---|
| cartridge holder | 10 |
| adapter | 11 |
| external thread | 12 |
| drug cartridge | 13 |
| distal end | 14 |
| cavity | 15 |
| septum | 17 |
| ferrule | 18 |
| distal wall | 19 |
| drug delivery device | 20 |
| interface | 200 |
| neck | 202 |
| cavity | 206 |
| distal needle portion | 210 |
| proximal needle portion | 212 |
| distal assembly portion | 216 |
| proximal assembly portion | 218 |
| longitudinal axis | 220 |

The invention claimed is:

1. A vial spiking device comprising:
a housing substantially surrounding a needle and at least partially defining a cavity configured to receive a portion of a drug vial, wherein the needle is partially received in the housing such that a portion of the needle is located in the housing and a portion of the needle projects out of the housing; and
a fluid flow sensor arranged in the housing and positioned outside the needle, adjacent to the portion of the needle located in the housing,
wherein the needle comprises a distal needle portion and a proximal needle portion and between the distal needle portion and the proximal needle portion a detection section.

2. The vial spiking device of claim 1, wherein the housing further comprises a central boss extending from an external surface of the housing, the central boss enclosing at least a portion of the needle.

3. The vial spiking device of claim 2, wherein at least a portion of the central boss includes a transparent material.

4. The vial spiking device of claim 2, wherein the central boss is non-metallic.

5. The vial spiking device of claim 3, wherein the fluid flow sensor is positioned adjacent to the needle in a manner such that the fluid flow sensor is aligned with the transparent material of the central boss.

6. The vial spiking device of claim 1, wherein the fluid flow sensor is positioned within the needle assembly adjacent to the detection section.

7. The vial spiking device of claim 1, wherein the needle comprises two coaxial needles axially separated by the detection section.

8. The vial spiking device of claim 1, wherein the detection section is formed from a material that is different from the distal needle portion and the proximal needle portion.

9. A drug delivery device, comprising:
a housing substantially surrounding a needle and at least partially defining a cavity configured to receive a portion of a drug vial, wherein the needle is partially received in the housing such that a portion of the needle is located in the housing and a portion of the needle projects out of the housing;
a drug vial positioned at least partly within the cavity;
a fluid flow sensor arranged in the housing and positioned outside the needle, adjacent to the portion of the needle located in the housing; and
a control unit in communication with the fluid flow sensor,
wherein the needle comprises a distal needle portion and a proximal needle portion and between the distal needle portion and the proximal needle portion a detection section.

10. The drug delivery device of claim 9, wherein the fluid flow sensor is positioned within the needle assembly adjacent to the detection section.

11. The drug delivery device of claim 9, wherein the detection section is formed from a material that is different from the distal needle portion and the proximal needle portion.

12. The drug delivery device of claim 9, wherein the drug vial contains a drug.

13. The drug delivery device of claim 12, wherein the drug comprises insulin, GLP-1, or both.

14. A vial spiking device comprising:
a housing substantially surrounding a needle and at least partially defining a cavity configured to receive a portion of a drug vial; and
a fluid flow sensor positioned adjacent to at least a portion of the needle within the housing,
wherein the needle comprises a distal needle portion and a proximal needle portion and between the distal needle portion and the proximal needle portion a detection section,
wherein the needle comprises two coaxial needles axially separated by the detection section.

* * * * *